(12) United States Patent
Epperly

(10) Patent No.: US 9,204,910 B2
(45) Date of Patent: Dec. 8, 2015

(54) TELESCOPING BONE SCREW

(75) Inventor: Scott Epperly, Torrance, CA (US)

(73) Assignee: Advanced Orthopaedic Solutions, Inc., Torrance, CA (US)

(*) Notice: Subject to any disclaimer, the term of this patent is extended or adjusted under 35 U.S.C. 154(b) by 354 days.

(21) Appl. No.: 13/045,470

(22) Filed: Mar. 10, 2011

(65) Prior Publication Data

US 2012/0059428 A1 Mar. 8, 2012

Related U.S. Application Data

(60) Provisional application No. 61/312,251, filed on Mar. 10, 2010.

(51) Int. Cl.
*A61B 17/56* (2006.01)
*A61B 17/72* (2006.01)

(52) U.S. Cl.
CPC ......... *A61B 17/7233* (2013.01); *A61B 17/7225* (2013.01); *A61B 17/7266* (2013.01)

(58) Field of Classification Search
CPC ......... A61B 17/42; A61B 17/44; A61B 17/46
USPC .................. 606/62–68, 79–85, 96–98, 104, 606/300–321
See application file for complete search history.

(56) References Cited

U.S. PATENT DOCUMENTS

| | | | |
|---|---|---|---|
| 2,397,545 A | 4/1946 | Hardinge | |
| 2,801,631 A | 8/1957 | John | |
| 4,621,629 A | 11/1986 | Koeneman | |
| 4,622,959 A | 11/1986 | Marcus | |
| 4,641,640 A | 2/1987 | Griggs | |
| 4,940,467 A | 7/1990 | Tronzo | |
| 5,032,125 A * | 7/1991 | Durham et al. | 606/62 |
| 5,041,116 A | 8/1991 | Wilson | |
| 5,122,133 A | 6/1992 | Evans | |
| 5,976,139 A * | 11/1999 | Bramlet | 606/66 |
| 7,503,919 B2 | 3/2009 | Shaw | |
| 2005/0010224 A1 | 1/2005 | Watkins et al. | |
| 2007/0260248 A1 | 11/2007 | Tipirneni | |
| 2008/0255559 A1 | 10/2008 | Leyden et al. | |
| 2009/0069813 A1 * | 3/2009 | von Hoffmann et al. | 606/65 |
| 2009/0254089 A1 | 10/2009 | Tipirneni et al. | |
| 2010/0312245 A1 | 12/2010 | Tipirneini et al. | |

FOREIGN PATENT DOCUMENTS

DE 19723339 A1 12/1998

* cited by examiner

*Primary Examiner* — Matthew Lawson
(74) *Attorney, Agent, or Firm* — Burgess Law Office, PLLC

(57) ABSTRACT

A bone screw for treating a bone fracture having a plunger assembly and a detent assembly on a body portion thereof. The detent assembly includes a detent member that is movable between a first and second position. The plunger assembly includes a threaded engagement portion and a plunger portion. The plunger portion is slidably disposed within a chamber of the body. The detent assembly operative to secure the body whereby said plunger portion moves independent of said body.

18 Claims, 15 Drawing Sheets

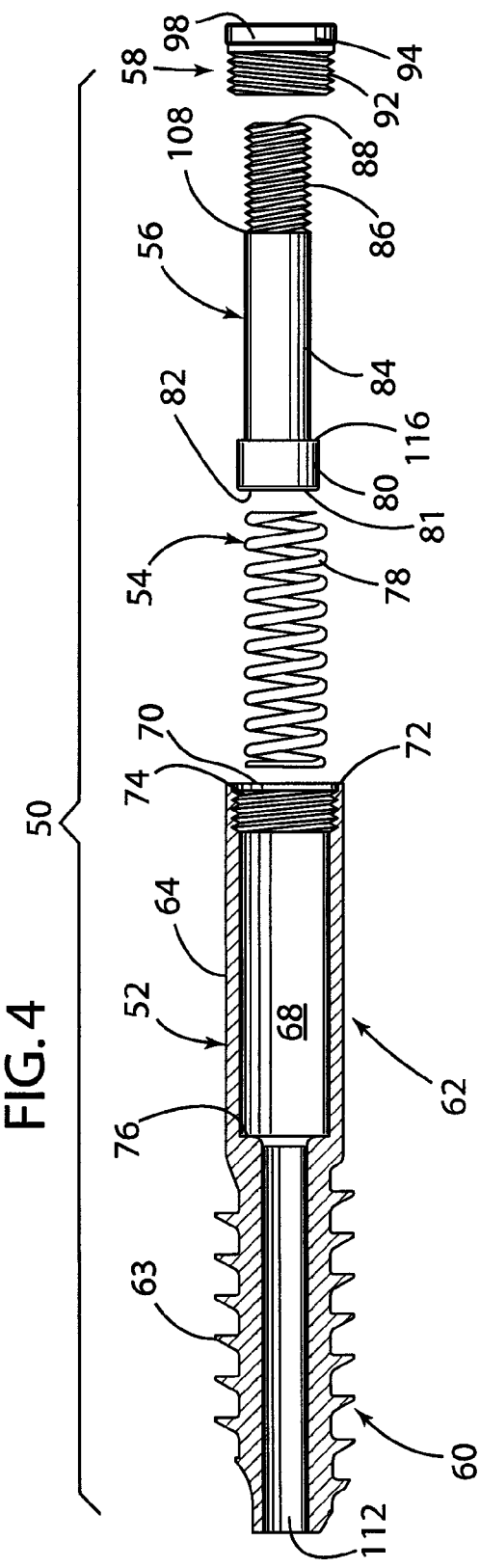
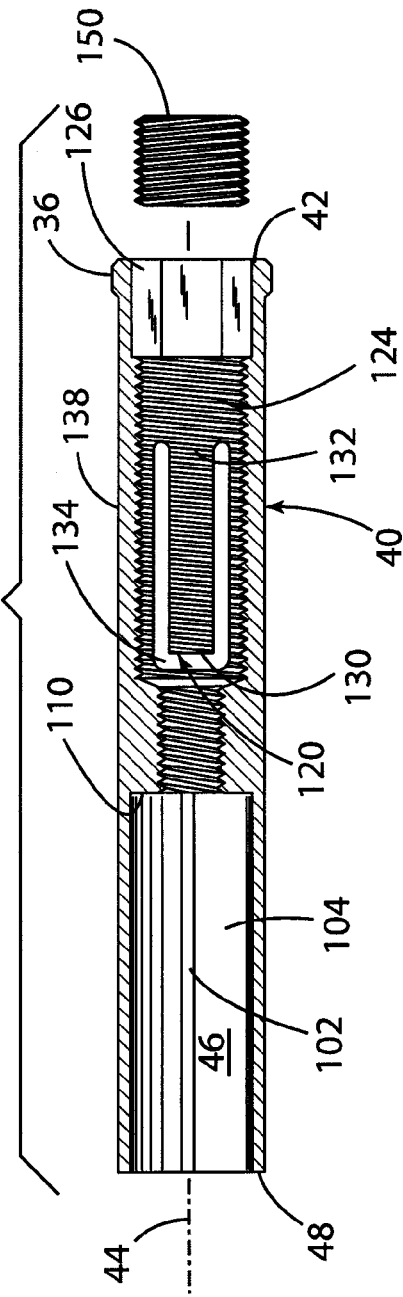
FIG. 4
FIG. 5

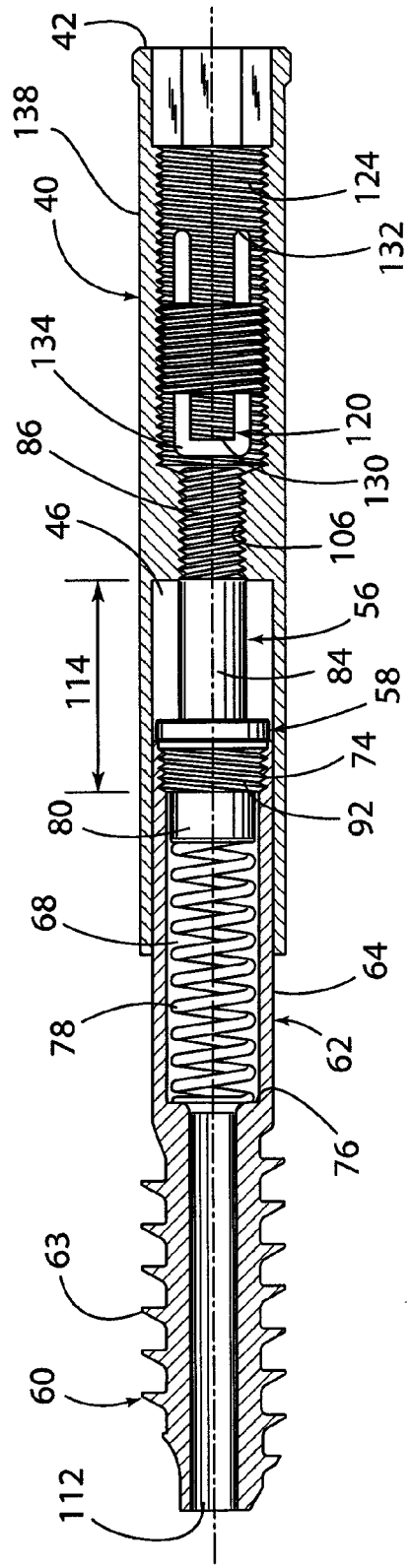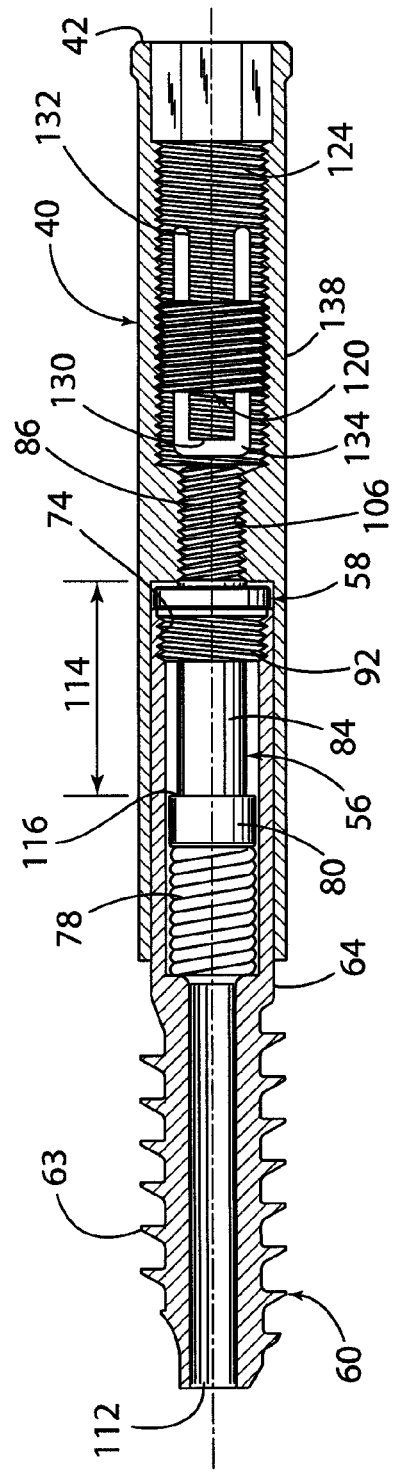
FIG. 6
FIG. 7

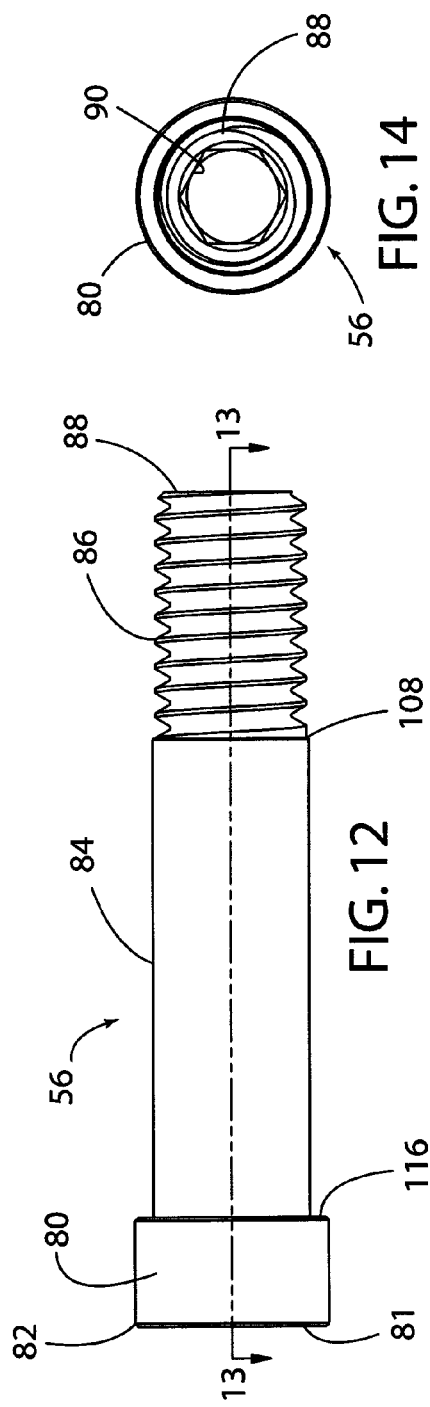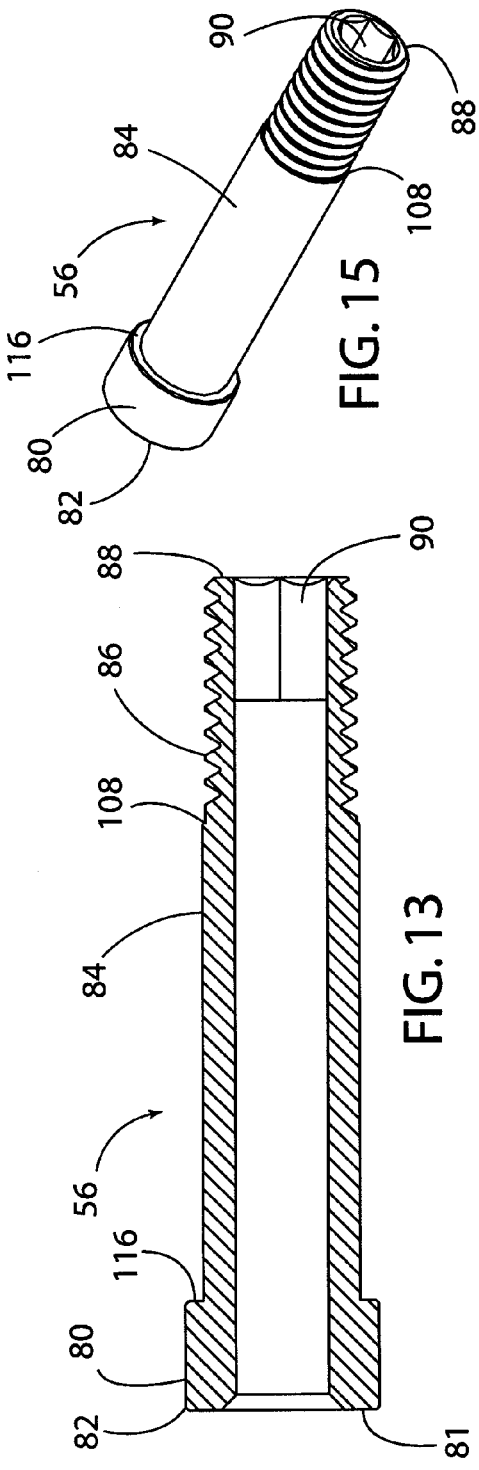

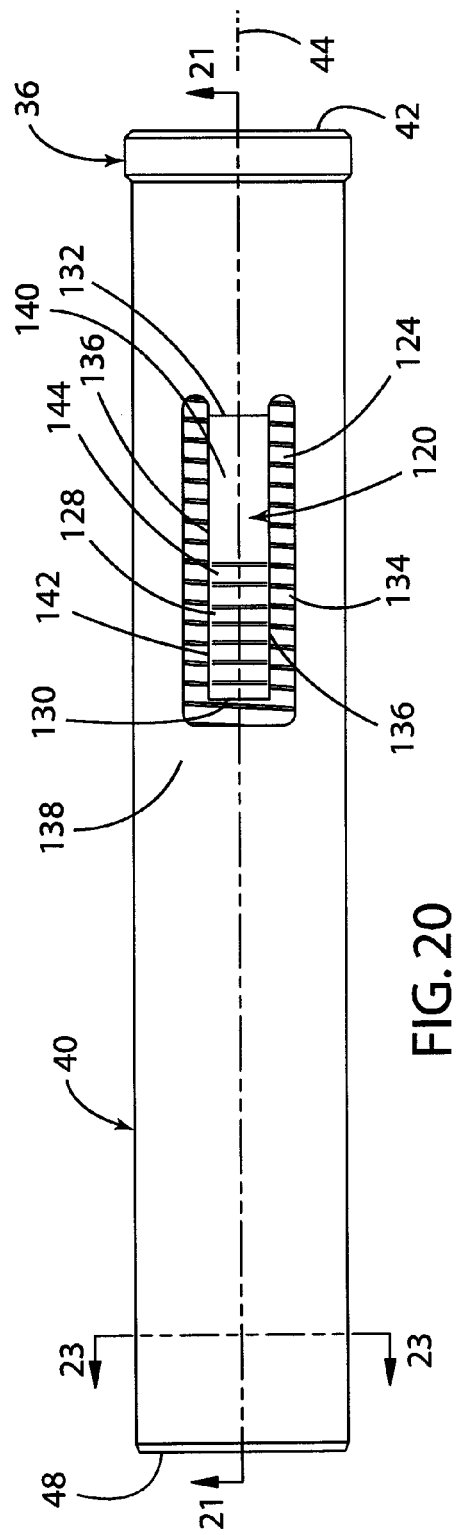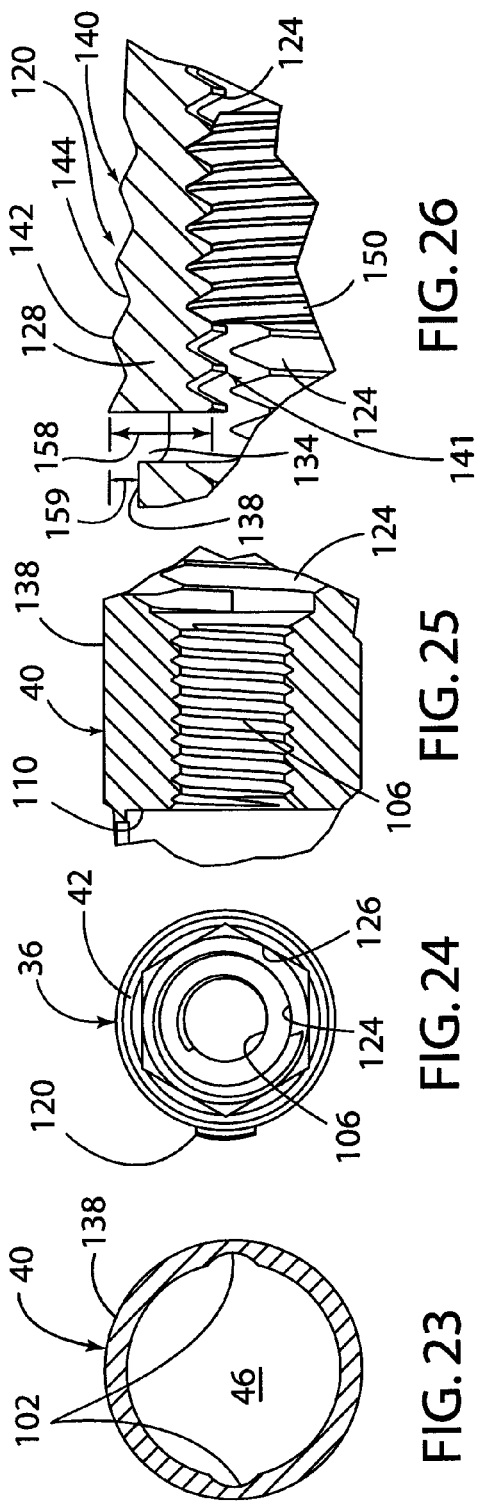
FIG. 20  FIG. 26  FIG. 25  FIG. 24  FIG. 23

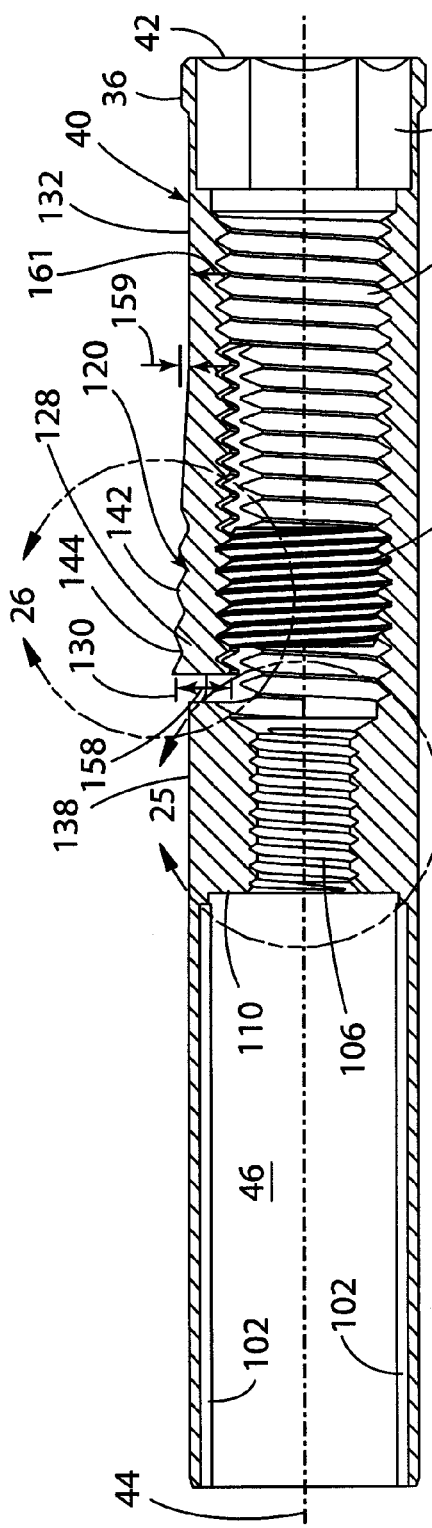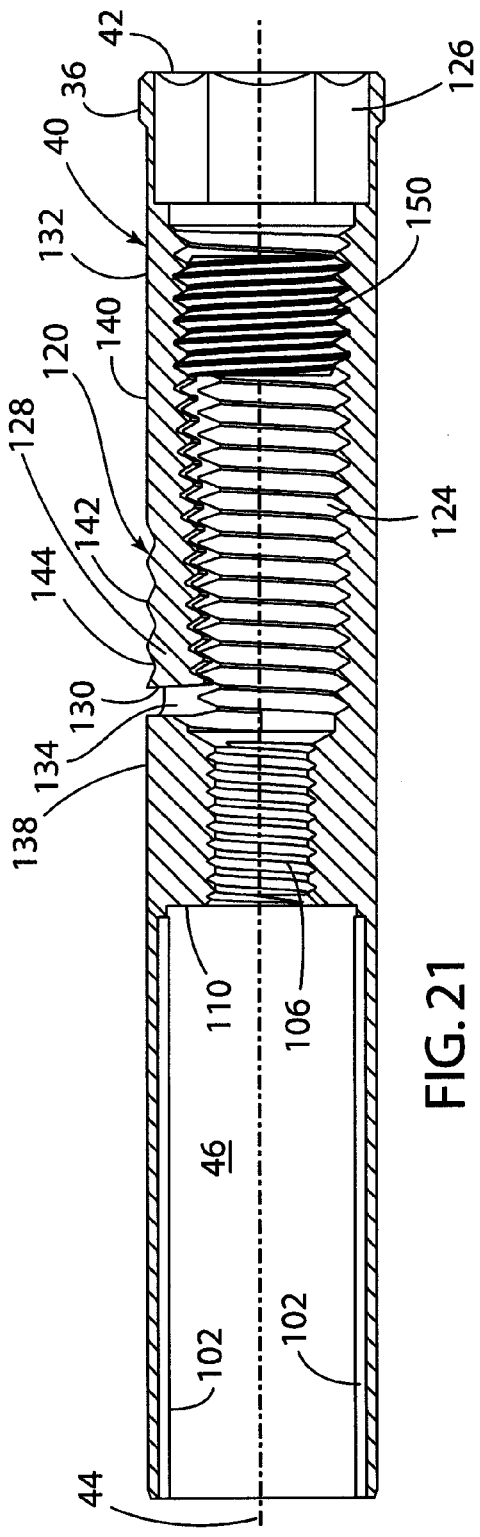

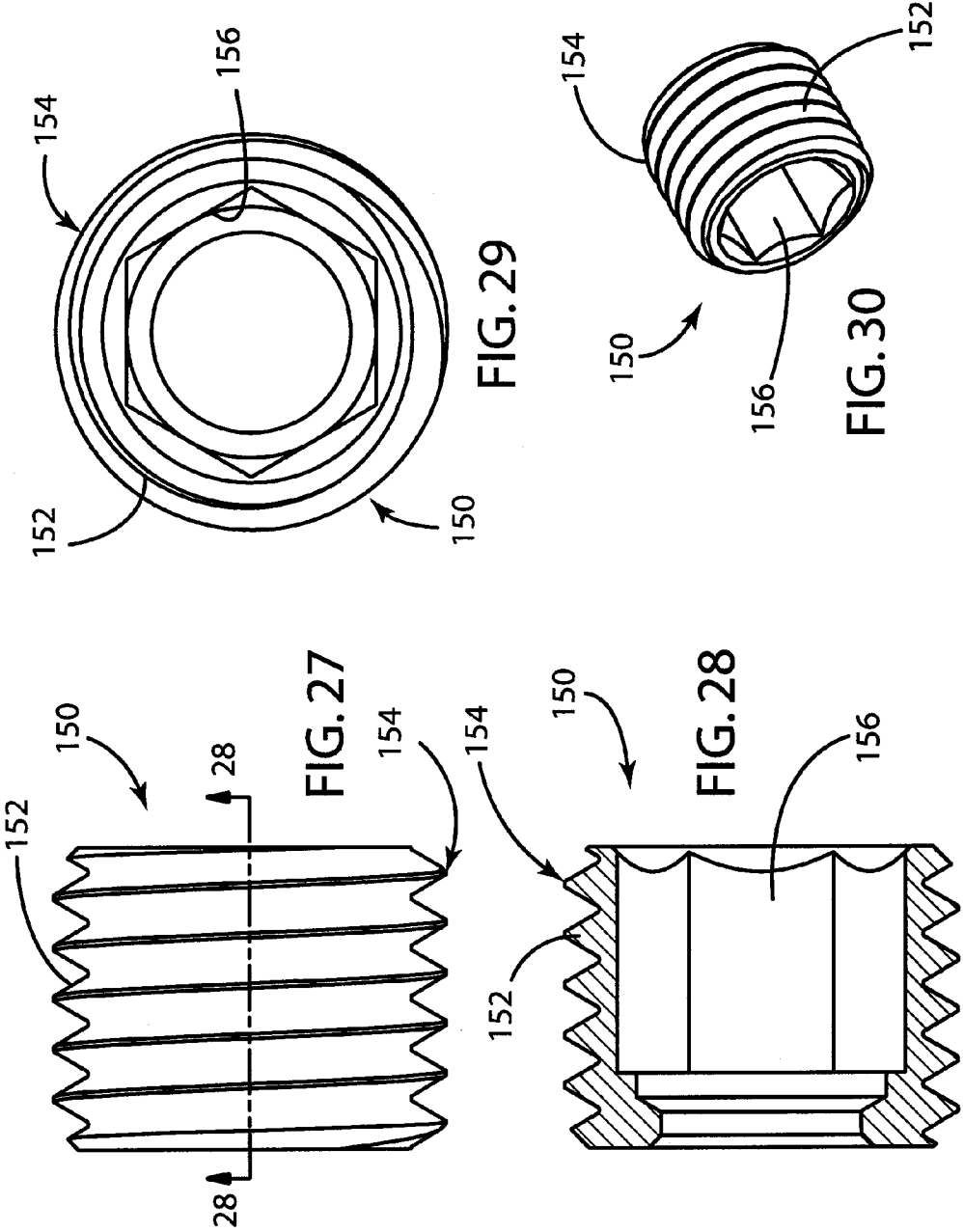

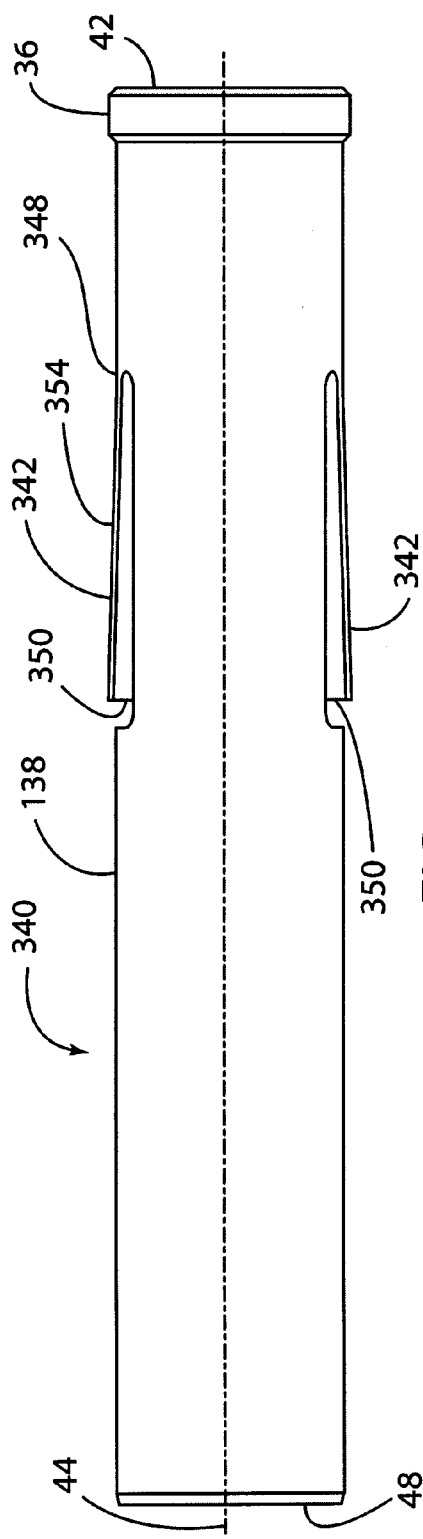
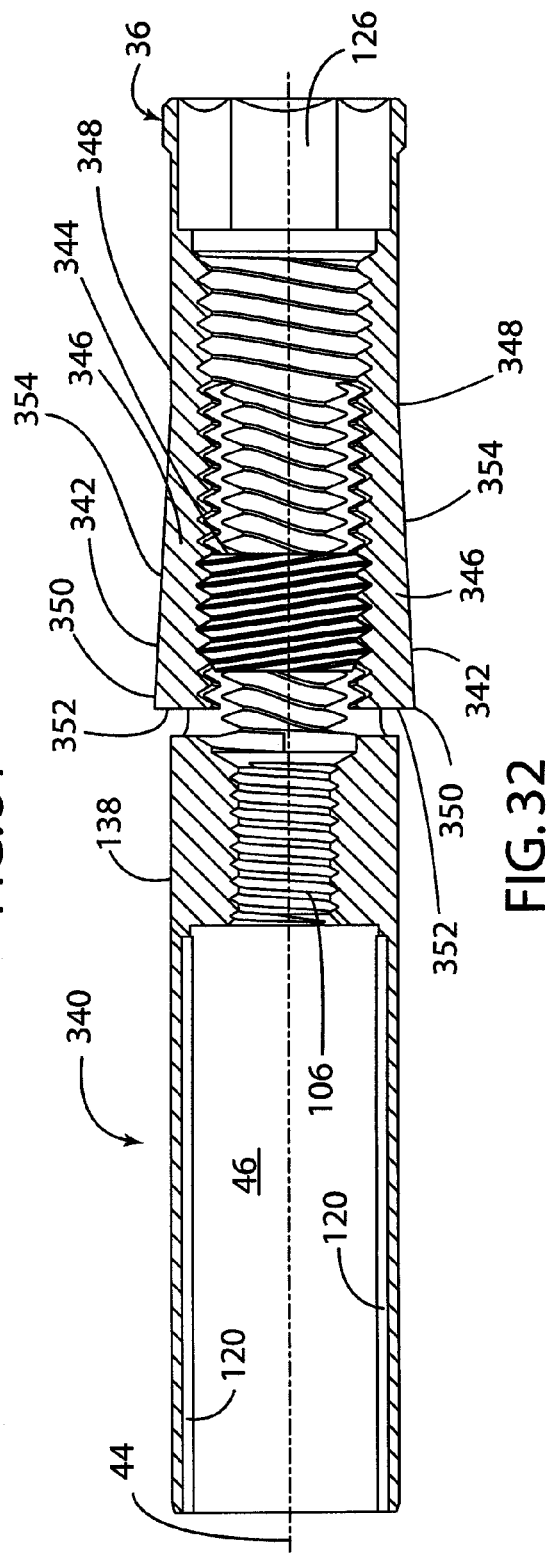
FIG.31
FIG.32

TELESCOPING BONE SCREW

CROSS-REFERENCE TO RELATED APPLICATIONS

This application benefit of U.S. Provisional Application Ser. No. 61/312,251 filed Mar. 10, 2010.

STATEMENT REGARDING FEDERALLY SPONSORED RESEARCH OR DEVELOPMENT

Not Applicable.

BACKGROUND OF THE INVENTION

1. Field of the Invention

The present disclosure relates generally to bone treatment devices, and more particularly to a bone screw used to treat a bone fracture wherein the bone screw is suitable for treating fractures of the femur including trochanteric, intertrochanteric and femoral neck fractures.

2. Description of Related Art

Orthopedic fixation systems used for stabilizing a fracture often include an internal fixation device, typically an elongated implant such as a nail, screw or pin, inserted into the intramedullary canal of the bone to stabilize the fracture and promote healing. Such fixation systems are suitable for use in treating fractures of the neck, head, intertrochanter, subtrochanteric, pathologic and certain ipsilateral shaft and neck fractures of the femur. The femur generally includes an elongated shaft, a ball shaped head that fits into the hip socket and a neck connecting the ball to the shaft. The shaft also includes a greater trochanter and a lesser trochanter.

For example, if the neck of the femur sustains a fracture a bone nail is inserted into the intramedullary canal and a bone screw inserted through an aperture in the head of the nail. The bone screw spans the fracture and threadably engages the femoral head. Typically, a smooth bore forms the aperture in the end of the nail. The bone screw extends through the smooth bore and rotates as it threadably engages the femoral head. Once the bone screw is suitably tightened, it is left in place during the healing process. In some instances, for example when the patient puts weight on the hip, the fracture will compress or settle. Thus, bone screw migration is one problem that may occur during the healing process. Specifically, when the patient puts weight on the hip the femoral head may move with respect to the femur; that is, the femoral head may slide medially or laterally at the fracture. The movement may be due to weakness in the bone, bone deterioration, misalignment of the fracture or other factors.

Depending upon the type of connection or engagement between the bone screw and the bone nail, movement of the femoral head with respect to the femur may result in "cut-out," that is the externally threaded end of the bone screw cuts or extends through the femoral head. Cut-out may occur when the bone screw is fixedly secured to the bone nail and does not move in the aperture. As the femoral head moves, due to settlement of the fracture or bone deterioration, it slides or travels along the bone screw. Eventually the femoral head moves close enough to the femur that the threaded end of the bone screw breaks through or pierces the femoral head and extends into the hip joint.

If the bone screw is slidably fixed in the aperture, that is the bone screw is constrained against rotation but is allowed to slide longitudinally in the smooth bore of the aperture, compression of the fracture may cause the head of the bone screw to extend outward significantly past the outer surface of the femur creating a raised surface that can cause pain at the hip joint. In addition, leaving the bone screw free to move with respect to the bone nail may cause the bone screw to migrate or loosen, thus creating a risk of failure at the fracture.

The features and advantages of the disclosure will be set forth in the description which follows, and in part will be apparent from the description, or may be learned by the practice of the disclosure without undue experimentation. The features and advantages of the disclosure may be realized and obtained by means of the instruments and combinations particularly pointed out in the appended claims.

SUMMARY OF THE INVENTION

An apparatus for repairing a bone fracture comprising a bone screw having a body. The body having a socket formed in one end thereof with a plunger assembly disposed in the socket. The body further includes a detent assembly, the detent assembly including a detent member operable to move between a first position and a second position wherein positioning the detent member in the second position secures the body whereby the plunger assembly includes a plunger portion that moves independent of the body.

The detent assembly further including a drive assembly illustrated in one embodiment as a screw member operative to move the detent member from the first position to the second position. The screw member threadably received in a threaded bore located within the body.

The detent member further having a variable thickness, the thickness increasing adjacent a free end of the detent member whereby the drive assembly engages the detent member and urges the free end of the detent member outward past the outer surface of the body.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The features and advantages of the disclosure will become apparent from a consideration of the subsequent detailed description presented in connection with the accompanying drawings in which:

FIG. 4 is an exploded cross-sectional side view of a plunger assembly for use with a bone screw in accordance with one embodiment of the present invention;

FIG. 5 is an exploded cross-sectional side view of a body for use with a bone screw in accordance with one embodiment of the present invention;

FIG. 6 is a cross-sectional side view of a bone screw according to the present invention with the plunger assembly extended;

FIG. 7 is a cross-sectional side view of a bone screw according to the present invention with the plunger assembly compressed;

FIG. 12 is a side view of a guide member for use with a bone screw according to the present invention;

FIG. 13 is a cross-sectional view of the guide member of FIG. 12 taken along line 13-13;

FIG. 14 is an end view of the guide member of FIG. 12;

FIG. 15 is a perspective view of the guide member of FIG. 12;

FIG. 20 is a side view of a body for use with a bone screw according to the present invention;

FIG. 21 is a cross-sectional side view of a body for use with a bone screw according to the present invention illustrating a detent member positioned flush with the outer surface of the body taken along lines 21-21 of FIG. 20;

FIG. 22 is a cross-sectional side view, similar to that shown in FIG. 21, of a body for use with a bone screw illustrating the detent member extending outwardly past the outer surface of the body;

FIG. 23 is a cross-sectional view of one end of the body of FIG. 22 taken along the lines 23-23;

FIG. 24 is an end view of the body of FIG. 22;

FIG. 25 is an enlarged cross-sectional area taken within the circle 25 of FIG. 22;

FIG. 26 is an enlarged cross-sectional area taken within the circle 26 of FIG. 22;

FIG. 27 is a side view of a set screw for use with a bone screw according to the present invention;

FIG. 28 is a cross-sectional view taken along lines 28-28 of FIG. 27;

FIG. 29 is an end view of the set screw of FIG. 27;

FIG. 30 is a perspective view of the set screw of FIG. 27;

FIG. 31 is a side view of an alternative embodiment of a body for use with a bone screw according to the present invention;

FIG. 32 is a cross-sectional view of the body of FIG. 31;

DETAILED DESCRIPTION OF THE PREFERRED EMBODIMENTS

Figures 1, 2:
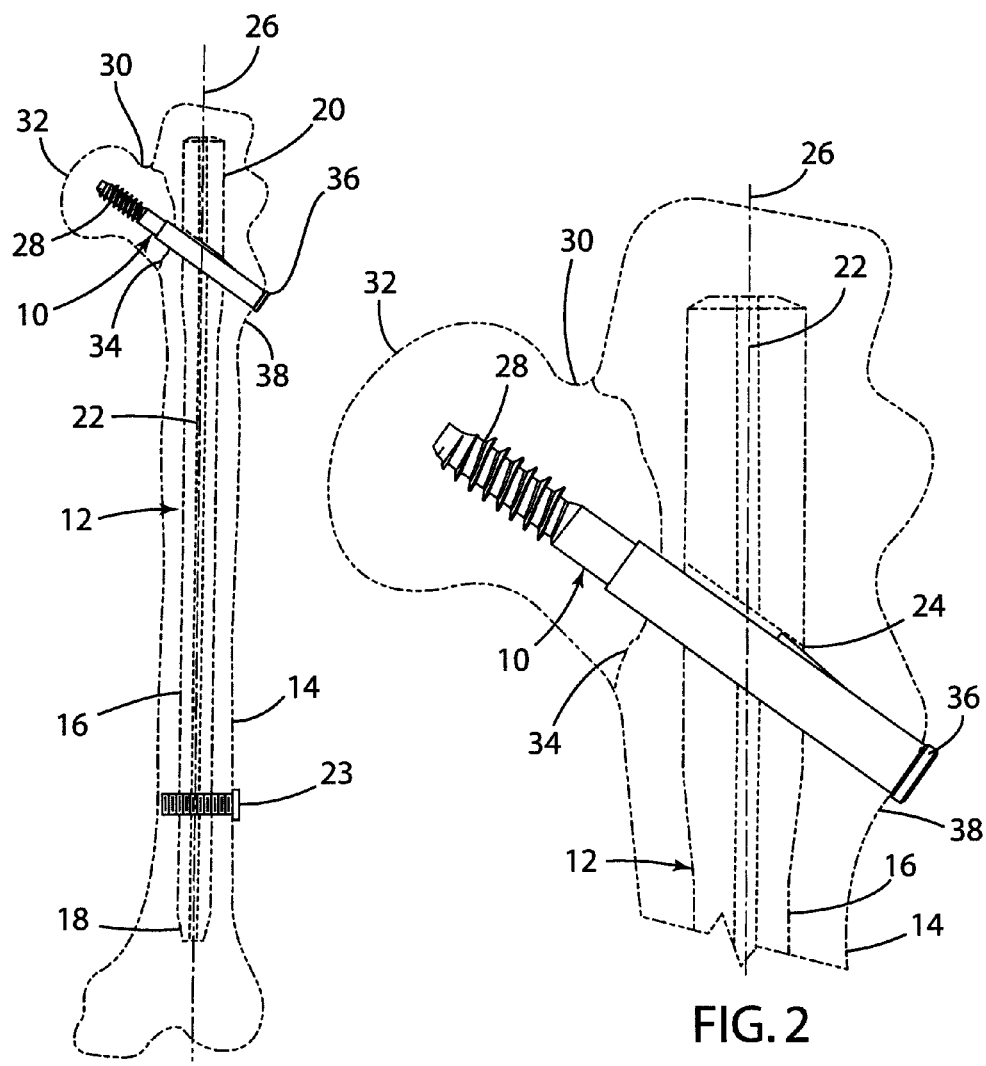
FIG. 1 is a schematic view of a bone screw according to one embodiment of the present invention shown as part of a fixation system placed in an assembled condition within a long bone such as a femur.
FIG. 2 is an enlarged schematic view of a bone screw according to one embodiment of the present invention shown extending through the proximal end of a bone nail placed in a femur.

The following description of the preferred embodiment(s) is merely exemplary in nature and is in no way intended to limit the invention, it's application, or uses.

For the purposes of promoting an understanding of these principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art having possession of this disclosure, are to be considered within the scope of the disclosure claimed.

Before the present apparatus and methods for treating a bone fracture are disclosed and described, it is to be understood that this disclosure is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present disclosure will be limited only by the appended claims and equivalents thereof.

It must be noted that, as used in this specification and the appended claims, the singular forms "a", "an", and "the" include plural referents unless the context clearly dictates otherwise. Moreover, as used herein, the terms "comprising", "including", "containing", "characterized by" and grammatical equivalents thereof are inclusive or open-ended terms that do not exclude additional, unrecited elements or method steps. In addition, the term "at" when referring to the location or placement of an element or object means in, near or by the area or location occupied by the particular structure or element referred to.

As used herein, the term "proximal" shall refer broadly to the concept of a nearest portion.

As used herein, the term "distal" shall generally refer to the opposite of proximal, and thus to the concept of a further portion, or a furthest portion, depending upon the context.

FIGS. 1-2 show a schematic view of a bone screw, seen generally at 10, according to the present invention as part of a fixation system, seen generally at 12. The fixation system 12, according to one embodiment, is shown placed in an assembled condition within a bone, illustrated here as a femur 14. The fixation system 12 includes a bone nail 16 having a distal end 18 and a proximal end 20. A passageway 22 extends longitudinally through the bone nail 16 between the proximal end 20 and the distal end 18. The passageway 22 receives insertion and extraction instrumentation, such as a guide wire (not shown), used to position the bone nail 16 within the femur 14. Typically, the distal end 18 of the bone nail 16 is inserted into the femur 14 first and follows the path of the guide wire. Whereby, the bone nail 16 is inserted into the intramedullary cavity of the femur 14. One or more distal anchoring members 23 may be used to anchor the distal end 18 of the bone nail 16 in place. It will be understood that the anchoring members 23 may be screws or any other suitable variety of fastening mechanism known in the art for use with trochanteric nails. Accordingly, the shape, size and configuration of the anchoring members 23 may vary within the scope of the present disclosure. The term "nail" as used here refers to a connective orthopedic nail implant, including but not limited to a trochanteric nail for use in a femur, as well as any other connective implant device suitable for use in any bone of interest.

The proximal end 20 of the bone nail 16 includes an aperture or throughbore 24 extending through the proximal end 20 in a direction typically angled with respect to the longitudinal axis 26 of the bone nail 16. The bone screw 10 extends through the aperture 24 such that a threaded portion 28 of the bone screw 10 extends through the femoral neck 30 of the femur 14 and is seated within the dense cortical bone of the femoral head 32. The bone screw 10 preferably extends parallel to the longitudinal axis of the femoral head 32 and femoral neck 30 when extending through the aperture 24. The bone screw 10 spans the fracture illustrated as the jagged line 34 in the drawings.

During installation the bone screw 10 is tightened or rotated until the head 36 of the bone screw 10 engages the outer cortex 38 of the femur 14 whereby continued tightening or rotating of the bone screw 10 creates a force that draws the femoral head 32 toward the femur 14 and compresses the fracture 34. It will be understood that the bone screw 10 may be useful in other types of bones, in addition to femurs, with or without the bone nail 16 in accordance with the principles of the present disclosure. Further, additional embodiments of the present invention may include using the bone screw 10 of the present invention with other types of side plates or supporting or reinforcing members used in orthopedic fixation systems.

Figure 3:
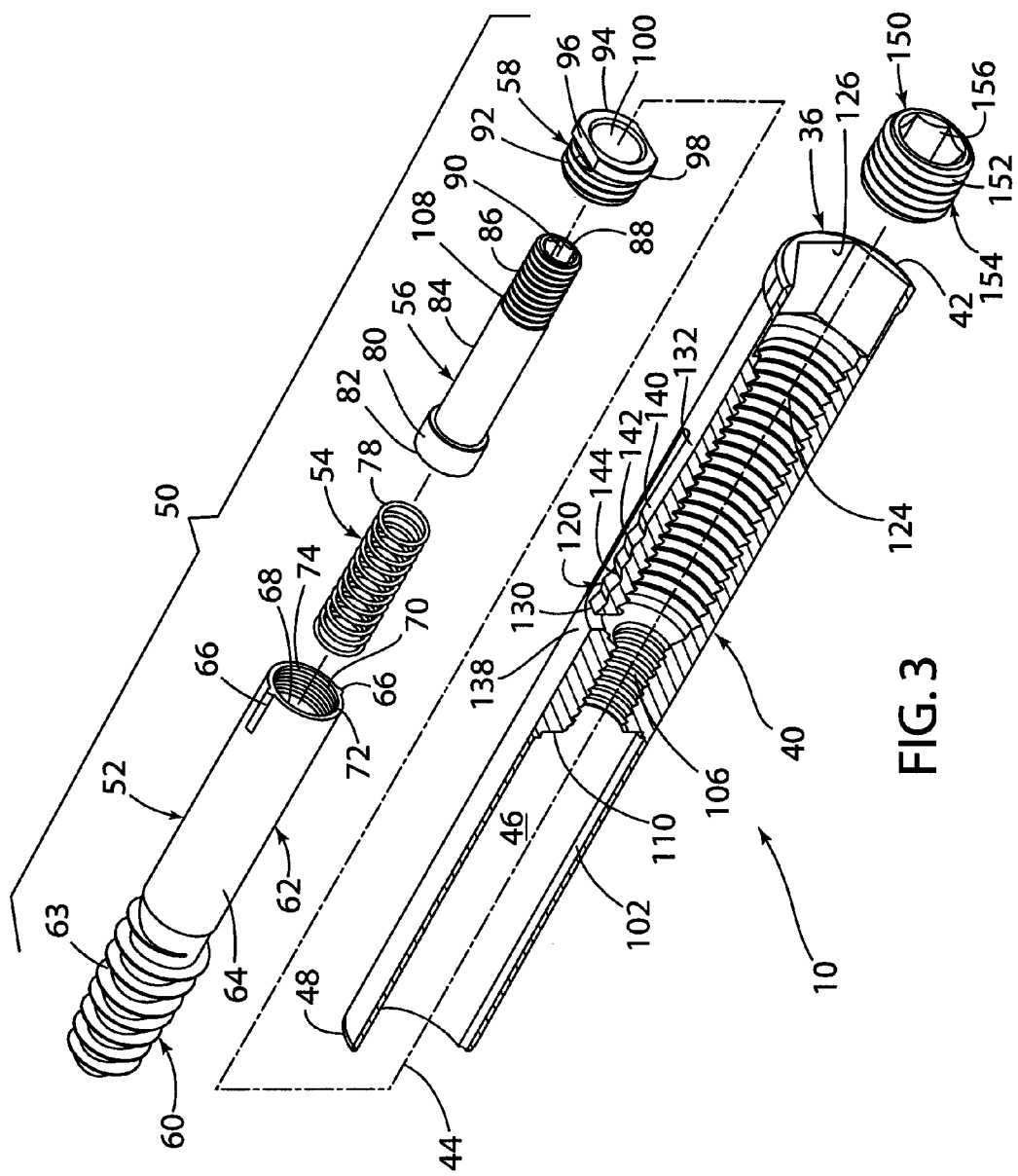
FIG. 3 is an exploded perspective view of a bone screw according to one embodiment of the present invention.

Referring now to FIG. 3, an exploded perspective view is shown of one embodiment of the bone screw 10 in accordance with the principles of the present invention. The bone screw 10 includes a cylindrical body or barrel 40 with the head 36 located at a first end 42 thereof. As illustrated, the head 36 is a lip or raised portion extending radially outward from the cylindrical body 40 of the bone screw 10. The head 36 operates as a stop or depth limiter whereby the head 36 of the bone screw 10 contacts or is seated on the outer cortex 38 of the femur 14.

The cylindrical body 40 includes several interior openings or apertures extending longitudinally along a longitudinal axis 44 of the bone screw 10. One of these interior openings is formed by a cylindrical shaped socket 46 that extends inwardly from a second end 48 of the cylindrical body 40. The socket 46 is sized to receive a plunger assembly 50 including a threaded plunger 52, a spring member 54, a guide member 56 and a retainer 58.

Turning for a moment to the plunger assembly 50, the threaded plunger 52 has a cylindrically shaped body including a threaded engagement portion 60 and a plunger portion 62. As illustrated, in FIGS. 4 and 9-11 the plunger portion 62 has a generally smooth cylindrical outer circumferential surface 64 located adjacent the threaded engagement portion 60. The threaded engagement portion 60 includes a plurality of helical threads 63. The helical threads 63 utilize a thread profile typical for use with bone screws. Detent tabs 66 extend radially outward from the cylindrical outer circumferential surface 64 of the plunger portion 62. While shown with two detent tabs 66 positioned generally opposite one another, a single or additional detent members can also be used.

The threaded plunger 52 further includes a generally cylindrical interior cavity or chamber 68 forming an opening 70 on one end 72 of the plunger portion 62. The chamber 68 includes a plurality of internal threads 74 extending into the chamber 68 from the end 72 of the plunger portion 62. The chamber 68 forms a generally cylindrical bore extending inward into the plunger portion 62 and terminating at a stop surface 76. In the present embodiment, the spring member 54 is shown as a coiled compression spring 78 sized to fit within the chamber 68.

As illustrated in FIGS. 3-4 and 12-15 the guide member 56 of the plunger assembly 50 has a generally cylindrical head 80 located on one end 82 thereof. That head 80 having a radially extending flat front face 81. The guide member 56 further includes a shank portion 84 connected to the head 80. The shank portion 84 being generally cylindrical and having a plurality of threads 86 located adjacent an end 88 opposite the head 80. A hexagonal shaped drive socket 90 is located in the end 88 of the guide member 56. While shown as having a hexagonal shape, the drive socket 90 can be of various shapes including star or square provided they are suitable to accept a driving tool used to rotate the guide member 56.

As illustrated in FIGS. 3-4 and 16-19 the retainer 58 of the plunger assembly 50 includes a threaded portion 92 and a head 94. The threaded portion 92 having an outer diameter and thread configuration such that it is complementary to and threadably received in the threads 74 of the chamber 68 of the threaded plunger 52. The head 94 is generally cylindrical in shape and includes opposing flat surfaces 96 located on the outer peripheral surface 98 thereof. The retainer 58 further includes a cylindrical aperture or bore 100 that extends through the retainer 58.

As shown in FIG. 3 the plunger assembly 50 is generally assembled by inserting the coiled compression spring 78 into the chamber 68 of the threaded plunger 52 through the opening 70. The compression spring 78 extends between the stop surface 76 and the internal threads 74 located at the end 72 of the threaded plunger 52. The head 80 of the guide member 56 is inserted into the cavity or chamber 68 with the head 80 of the guide member 56 sized and shaped such that the head 80 slidably fits in the generally cylindrical cavity 68. For example, in the disclosed embodiment, the chamber 68 is generally cylindrically shaped and the head 80 of the guide member 56 is also generally cylindrically shaped. It should be understood however the other complementary configurations can also be used. Once the head 80 of the guide member 56 is placed in the chamber 68 and contacts the spring 78, the retainer 58 is placed over the guide member 56 by sliding the shank portion 84 of the guide member 56 through the aperture 100 of the retainer 58. The retainer 58 slides along the shank portion 84 until the threaded portion 92 of the retainer 58 engages the complementary threads 74 located in the opening 70 at the end 72 of the threaded plunger 52. The retainer 58 is then tightened using a suitable tool engaging the opposed flat surfaces 96 of the retainer 58 until the head 94 of the retainer 58 contacts and is secured to the end 72 of the threaded plunger 52. As illustrated in FIG. 6 in the expanded or uncompressed position the compression spring 78 forces the guide member 56 outward until the head 80 of the guide member 56 contacts the retainer 58.

Once assembled the plunger assembly 50 is then slidably secured in a non-rotatable telescopic relationship in the socket 46 of the body 40. As illustrated in FIGS. 3-5 and 22-23 the socket 46 of the body 40 includes a pair of opposed grooves or channels 102 extending radially outward from the inner circumferential surface 104 of the socket 46. The grooves 102 are sized such that they slidably receive the detent tabs 66 located on the threaded plunger 52. The grooves 102 and detent tabs 66 cooperate to prevent relative rotational movement between the plunger assembly 50 and the body 40 while allowing the plunger assembly 50 to move in a reciprocal or back and forth manner in the direction of the longitudinal axis 44 of the body 40.

As illustrated in FIGS. 6-7 the guide member 56 is used to secure the plunger assembly 50 to the body 40. To secure the plunger assembly 50 to the body 40, the plunger assembly 50 is inserted into the socket 46 with the detent tabs 66 placed in the grooves or channels 102 located in the socket 46. As illustrated in FIGS. 3-7, 20-22 and 25 the body 40 includes a threaded aperture 106 extending longitudinally along the longitudinal axis 44 of the body 40. The threads of the threaded aperture 106 are complementary to the threads 86 on the guide member 56. Accordingly, once the threads 86 of the guide member 56 contact the threaded aperture 106 a suitable drive tool (not shown) having a configuration complementary to the drive socket 90 located in the end 88 of the guide member 56, shown herein as having a hexagonal shape, is inserted into the body 40 from the first end 42 until it engages the drive socket 90 of the guide member 56. Rotating the drive tool rotates the guide member 56 until the shoulder 108 of the guide member 56 located between the threads 86 and the shank portion 84 is seated on the surface 110 forming the base or bottom of the socket 46.

FIGS. 3-7 also illustrate a second method for installing the guide member 56 in the threaded aperture 106, wherein a passageway 112 extends longitudinally through the threaded plunger 52 and a drive socket is formed on the front flat face 81 located on the end 82 of the head 80. Accordingly, a drive tool may extend through the passageway 112 and engage the drive socket formed in the front flat face 81 of the end 82 of the head 80 to rotate the guide member 56 and correspondingly secure the guide member 56 in the body 40.

FIGS. 6-7 show the bone screw 10 in accordance with one aspect of the present invention, the bone screw 10 fully extended as illustrated in FIG. 6 and fully compressed as illustrated in FIG. 7. The distance of travel 114 of the threaded plunger 52 with respect to the body 40 is determined by the distance between the stop surface 116, that is the shoulder formed at the junction of the shank portion 84 and the head 80 of the guide member 56, and the stop surface 110 formed at the bottom of the socket 46 of the body 40. Accordingly, varying the length of the shank portion 84, that is the distance between the stop surface 110 and the shoulder 108 of the guide member 56, varies the amount of travel and correspondingly the amount of longitudinal compression of the bone screw 10.

Varying the strength or spring constant k of the spring 78 varies the compressive force necessary to move the threaded plunger 52 through the distance of travel 114. For example, depending upon the weight and size of an individual and degree of severity of the fracture, the compressive force of the spring 78 can be changed or modified to provide a suitable resistance force. It should be understood that the resistance force need not be linear, but may vary over the distance of travel 114. Accordingly, the present invention allows for compression of a fracture when a load is applied, for example, when a patient stands and weight is transferred from the femoral head 32 to the femur 14, if necessary, the plunger assembly 50 allows movement of the threaded plunger 52 within the socket 46 of the body 40 enabling compression between the femoral head 32 and the femur 14. The preferred embodiment contemplates a distance of travel 114 of 10 mm, however this is for illustrative purposes only and the actual degree or distance of travel 114 may be greater or less than 10 mm.

As illustrated in FIGS. 1-5, 20-22 and 26 the bone screw 10 includes a detent member, seen generally at 120 and illustrated as a finger, that is driven radially outward by a drive assembly shown as a screw member or set screw 150. The detent member 120 engages the bone nail 16 and maintains a positional relationship between the body 40 of the bone screw 10 and the bone nail 16. The detent member 120 fixes the position of the body 40 of the bone screw 10 with respect to the bone nail 16 and prevents both sliding and rotating of the body 40 of the bone screw 10 with respect to the bone nail 16. Accordingly, the detent member 120 keeps the body 40 of the bone screw 10 in place while the plunger assembly 50 allows movement of the plunger member 52 independent of the body 40 whereby any compression or sliding between the femoral head 32 and femur 14 is compensated for by movement of the plunger assembly 50.

As illustrated, the body 40 includes a threaded bore 124 extending inwardly from the first end 42 toward the threaded aperture 106. As shown in the drawings the threaded aperture 106, which receives the guide member 56, is located between the first end 42 and the second end 48 of the body 40. An internal drive socket 126 is located adjacent the first end 42 of the body 40. As illustrated the drive socket 126 has a hexagonal configuration shaped to accept a hexagonal drive tool, see FIGS. 33-35 used to rotate and install the bone screw 10.

FIGS. 20-22 and 26 illustrate the detent member 120 in greater detail. The detent member 120 of the present embodiment is a cantilevered member 128 having a free end 130 and a fixed end 132. A slot 134 extends along the sides 136 and free end 130 of the cantilevered member 128. The free end 130 of the cantilevered member 128 is configured such that in the initial or first position it remains at or below the outer circumferential surface or periphery 138 of the body 40. As shown in the illustrated embodiment, the outer surface 140 of the detent number 120 may move radially outward to a position past or above the outer circumferential surface or periphery 138 of the body 40. The outer surface 140 of the cantilevered member 128 may include a plurality of ridges and grooves 142, 144. While the inner surface 141 of the cantilevered member 128 has a threaded configuration identical to the threads of the threaded bore 124.

Figure 8:
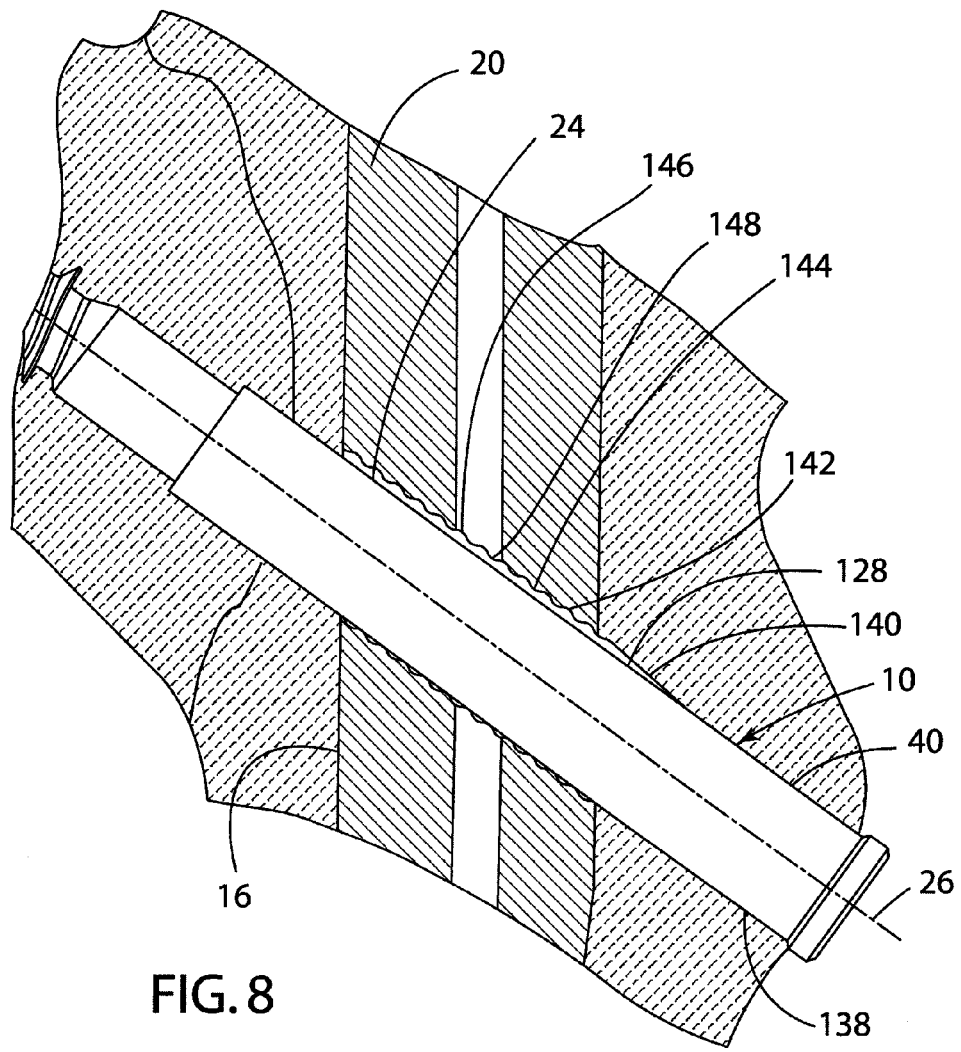
FIG. 8 is an enlarged schematic view of a bone screw according to a second embodiment of the present invention shown extending through the proximal end of a bone nail.
Figure 10:
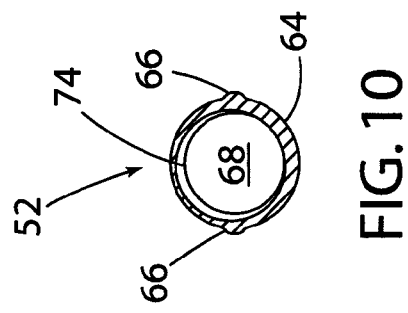
FIG. 10 is a cross-sectional view of the plunger of FIG. 9 taken along line 10-10.
Figure 9:
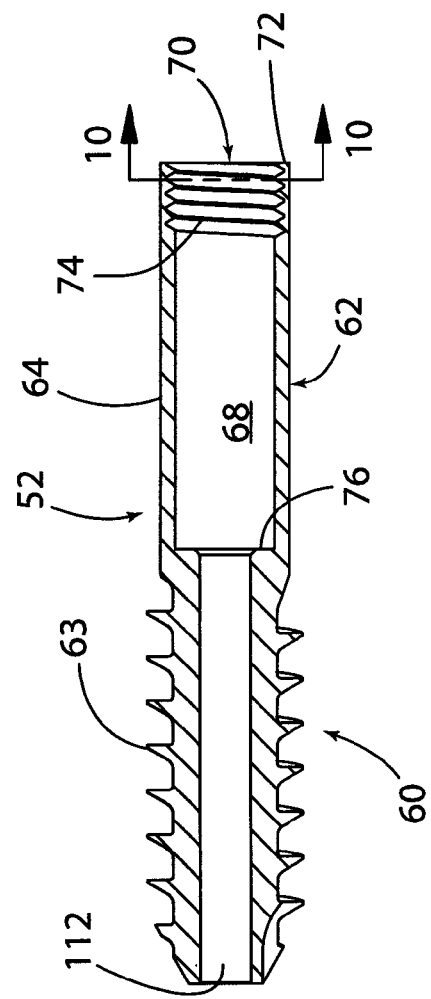
FIG. 9 is a cross-sectional view of the plunger of FIG. 11 taken along line 9-9.
Figure 11:
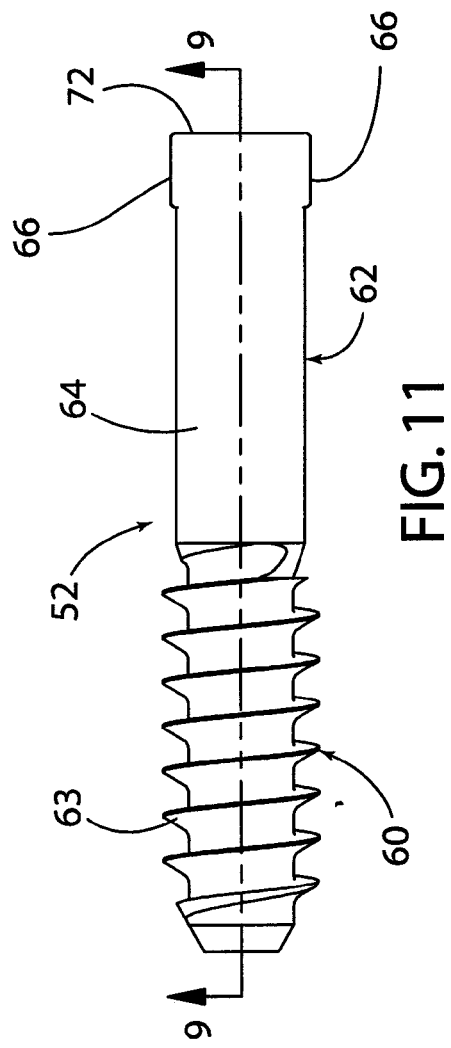
FIG. 11 is a side view of a plunger for use with a bone screw according to the present invention.
Figure 18:
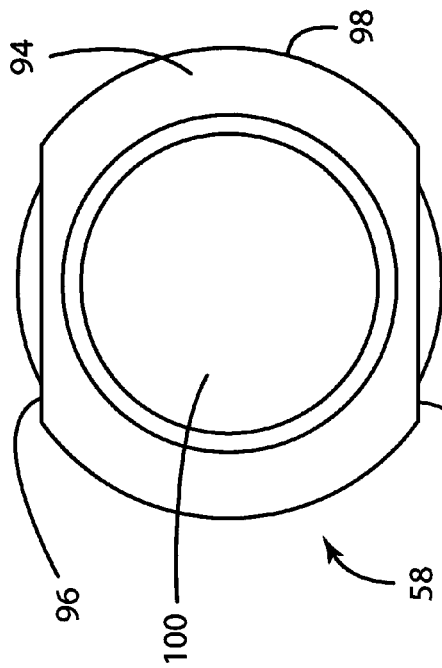
FIG. 18 is an end view of the retainer of FIG. 16.
Figure 19:
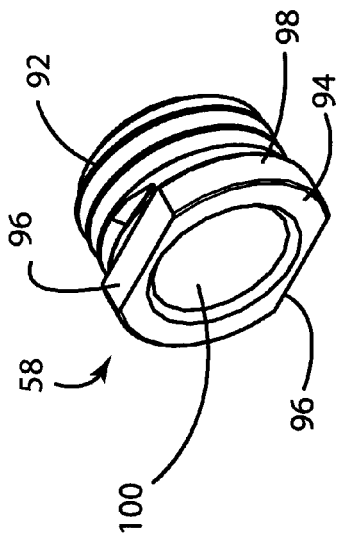
FIG. 19 is a perspective view of the retainer of FIG. 16.
Figure 16:
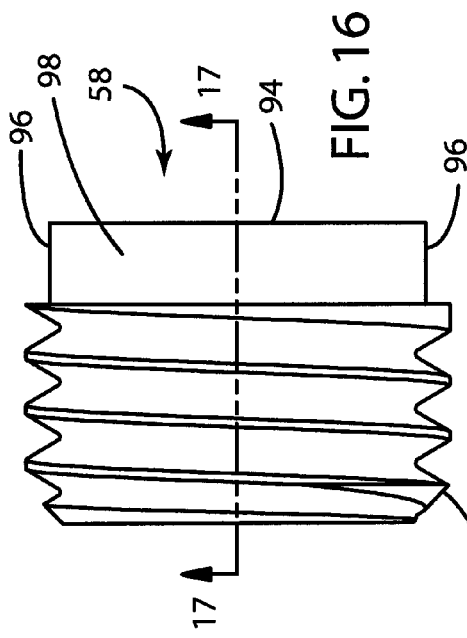
FIG. 16 is a side view of a retainer for use with a bone screw according to the present invention.
Figure 17:
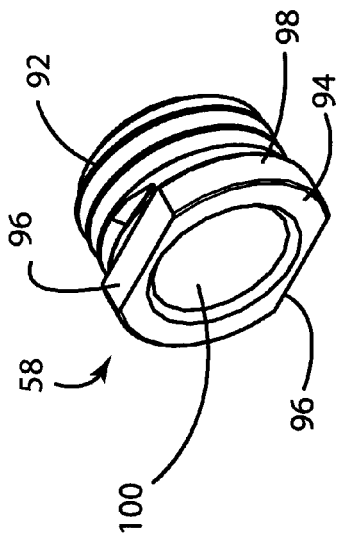
FIG. 17 is a cross-sectional view of the retainer of FIG. 16 taken along line 17-17.

As shown in FIG. 8 the plurality of ridges and grooves 142, 144 on the outer surface 140 of the cantilevered member 128 cooperate with corresponding and complementary ridges and grooves, 146 148 located in the aperture 24 extending through the proximal end 20 of the bone nail 16. While the cantilevered member 128 is disclosed with a plurality of ridges and grooves 142, 144 to aid in securing the bone screw 10 to the bone nail 16, this is but one embodiment. As illustrated in FIG. 2, the outer surface 140 of the cantilevered member 128 may be smooth with the corresponding interior surface of the aperture 24 in the proximal end 20 of the bone nail 16 also being smooth. Further, it is contemplated that the outer surface 140 of the cantilevered member 128 may include other configurations to increase the frictional or holding force between the detent member 120 and correspondingly the bone screw 10 and the bone nail 16. In addition, other surface configurations or coatings can be utilized to increase the holding force fixing the bone screw 10 in the aperture 24. While the outer circumferential surface or periphery 138 of the body 40 is disclosed herein without the ridges and grooves 142, 144 shown on the cantilevered member 128, the invention contemplates adding such ridges and grooves to the outer surface 138 of the body 40. Further, it is within the scope of the present invention to provide other types of surfaces or surface coatings that would reduce movement or rotation of the bone screw 10 with respect to the bone nail 16.

As illustrated in FIGS. 3, 20-22 and 26 one example of the drive assembly is shown in the present embodiment as a threaded member or set screw 150 having a plurality of threads 152 located on the outer peripheral surface 154 thereof wherein the set screw 150 threadably engages the threaded bore 124 of the body 40. The set screw 150 has a hexagonal bore 156 forming a drive socket suitable for receiving a driving tool, see FIGS. 33-35. The set screw 150 operates to urge the cantilevered member 128 radially outward as the set screw 150 travels inwardly along the threaded bore 124. The set screw 150 urges or drives the free end 130 of the cantilevered member 128 outwardly as it approaches the free end 130 since the wall or radial thickness 158 of the cantilevered member 128 is greater at the free end 130 of the cantilevered member 128 than the wall or radial thickness 161 at the fixed end 132 of the cantilevered member 128. Since the outer diameter of the set screw 150 remains constant, as it travels in the threaded bore 124 and along the length of the cantilevered member 128 it urges the free end 130 of the cantilevered member 128 outward whereby it extends above or past the outer peripheral surface 138 of the body 40 to a distance 159.

In one embodiment, the thickness of the free end 130 of the cantilevered member 128 is increased through the following steps, during manufacture of the body 40, the body 40 is turned to a predetermined outer diameter with a portion thereof, specifically the area where the cantilevered member 128 will be located, having a raised portion or section having a greater outer diameter. The magnitude or difference in the respective outer diameters being the amount or distance 159 that the free end 130 of the cantilevered member 128 will extend above or outwardly past the outer circumferential surface or periphery 138 of the body 40. In one embodiment, the raised section may have a conical shape beginning roughly at or corresponding to the location of the free end 130 of the cantilevered member 128 and tapering off to the overall diameter of the body 40 as it approaches the first end 42. Cutting the slot 134 forms the cantilevered member 128. Once formed, the cantilevered member 128 is depressed or forced inward into the threaded bore 124 while the remaining raised portion or section is removed whereby the entire outer circumferential surface or periphery 138 of the body 40 has a constant outer diameter. In the embodiment wherein the outer surface 140 of the cantilevered member 128 includes ridges and grooves 142, 144 these can be formed prior to cutting the slot 134 and moving the free end 130 of the cantilevered member 128 inward prior to removing the remaining raised portion or section. It is within the scope of the present invention to use other means to increase the thickness of the free end 130 of the cantilevered member 128 whereby as the set screw 150 travels through the threaded bore 124 it urges the free end 130 outwardly such that it engages the aperture 24 located in the proximal end 20 of the bone nail 16. For example, additional material could be added to the outer surface 140 of the cantilevered member 128 to increase its over all thickness.

Accordingly, the present invention contemplates a detent member 120 movable between a first position wherein the free end 130 of the cantilevered member 128 is positioned flush with or at the same level as the outer peripheral surface 138 of the body 40 and a second position wherein the free end 130 of the cantilevered member 128 extends above or past the outer peripheral surface 138 the body 40. While shown herein using a cantilevered member 128 formed as an integral part of the body 40, the present invention contemplates that the detent member 120 may also be inserted into the threaded bore 124 as a separate member wherein the separate member is still urged outwardly by the drive assembly and still come within the scope of the present invention.

Referring to FIGS. 31 and 32 there is shown an alternative embodiment of a body 340 for use with a bone screw 10 of the present invention. The body 340 includes first and second opposed detent members, seen generally at 342, urged outwardly by a set screw 344. The opposed detent members 342 are similar in design to those disclosed in the previous embodiment in that the detent members 342 include cantilevered members 346 having a fixed end and a free end 348, 350. The free end 350 once again having a wall or radial thickness 352 greater than the wall or radial thickness at the fixed end 348. The alternative embodiment also discloses the outer surface 354 of the cantilevered members 346 as smooth rather than with the ridges and grooves of the previous embodiment.

Figure 33:
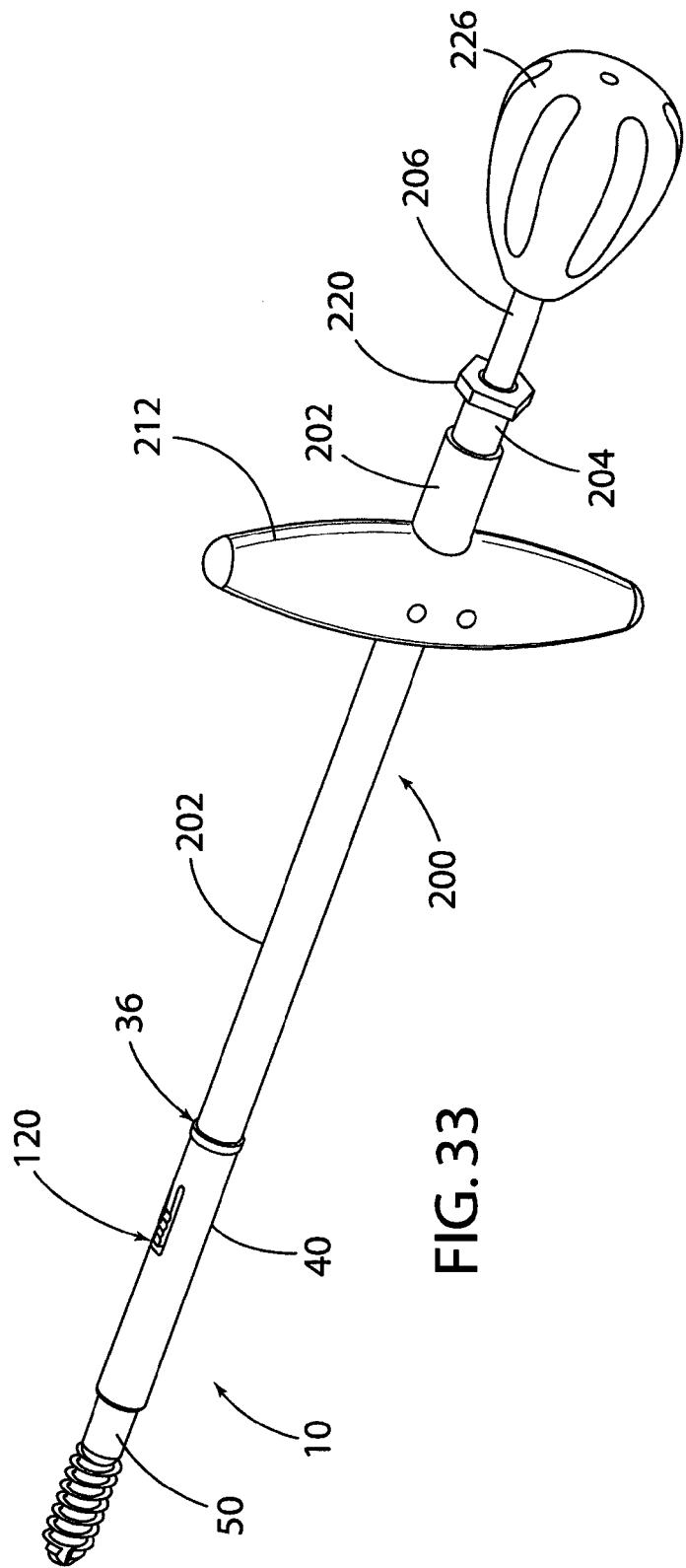
FIG. 33 is a perspective view of installation equipment used for installing a bone screw according to the present invention.
Figure 34:
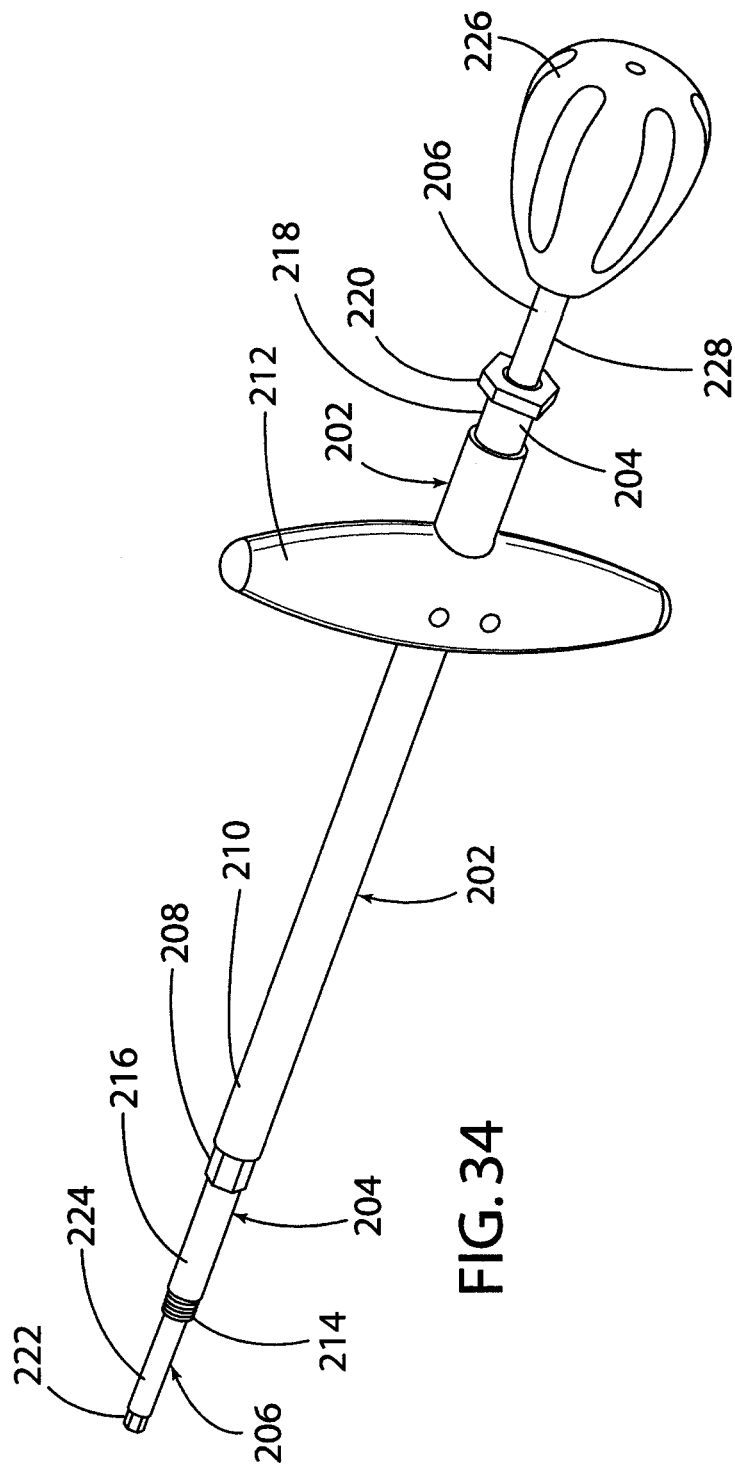
FIG. 34 is a perspective view of the installation equipment and the bone screw.
Figure 35:
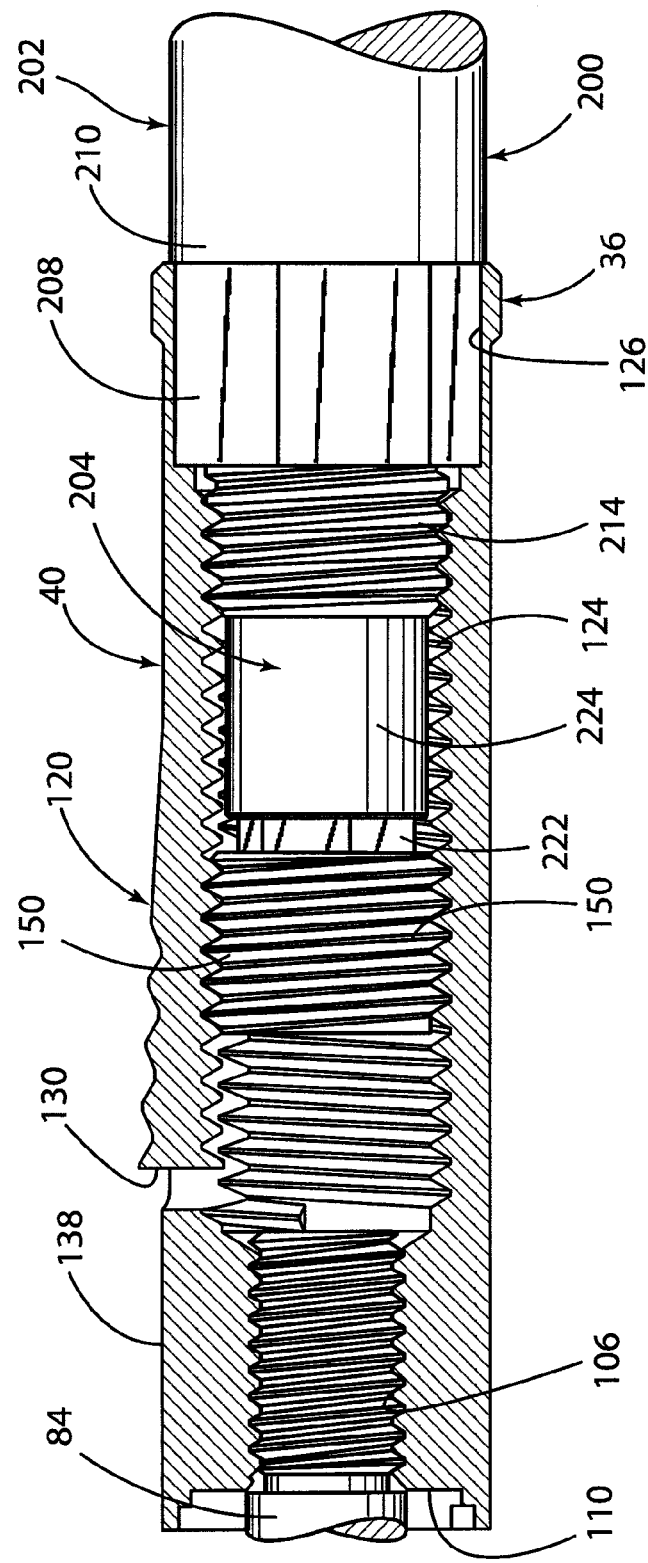
FIG. 35 is a cross-sectional view illustrating the installation equipment connected to the bone screw according to the present invention.

Turning now to FIGS. 33-35 an installation tool, seen generally at 200, for use in installing the bone screw 10 according to the present invention is shown. The installation tool 200 includes a first or outer drive member or driver 202, a second or middle drive member or driver 204 disposed within the first or outer drive member 202 and a third or inner drive member or driver 206 disposed within the second or middle drive member 204. The outer drive member 202 is a hollow rod or shaft having a hexagonal shaped drive portion 208 located on the end 210 thereof. A handle 212 is located at the opposite end and is attached to the outer driver 202 whereby rotation of the handle 212 rotates the outer driver 202. The middle driver 204 includes a threaded portion 214 located on an end 216 and the opposite end 218 of the middle driver 204 includes a head 220 configured to accept a tool used to rotate the middle driver 204 independent of the outer driver 202. The middle driver 204 is also a hollow member and the inner driver 206 is nested within the middle driver 204. A hexagonal shaped drive member 222 is attached to one end 224 with a handle 226 attached to the opposite end 228.

FIG. 35 illustrates the engagement between the installation tool 200 and the bone screw 10. Specifically, the threaded portion 214 of the middle driver 204 threadably engages the threaded bore 124 and a suitable drive tool (not shown) contacts the head 220 of the middle driver whereby the operator can tighten and securely attach the bone screw 10 to the installation tool 200. The outer driver 202 then slides over the middle driver 204 until the hexagonal shaped drive portion 208 engages the hexagonal shaped drive socket 126 of the bone screw 10. It should be understood that rotation of the handle 212 rotates the entire bone screw 10 such that the operator can properly insert the bone screw 10. Once the bone screw 10 is placed in its proper position within the femoral head 32, the inner driver 206 is then slid forward within the middle driver 204 until the hexagonal shaped drive portion 222 thereof engages the hexagonal shaped bore 156 of the set screw 150. Accordingly, rotation of the handle 226 attached to the inner driver 206 correspondingly rotates and moves the set screw 150 inwardly towards the free end 130 of the cantilevered member 128 whereby the operator forces or drives the detent member 120 outwardly into engagement with the aperture 24 located in the proximal end 20 of the bone nail 16. It should be understood that the handle 226 located on the inner driver 206 may have some type of torque limiting or clutch arrangement that limits the amount of torque applied to the set screw 150 which correspondingly limits the force generated by the detent member 120. While not necessary, it is contemplated that the use of such a torque limiting device or handle can be used to control the pressure applied by the detent member 120 and prevent over tightening and possible damage to the bone screw 10.

The description of the invention is merely exemplary in nature and, thus, variations that do not depart from the gist of the invention are intended to be within the scope of the invention. Such variations are not to be regarded as a departure from the spirit and scope of the invention.

What is claimed is:
1. An apparatus for repairing a bone fracture comprising:
   a body, said body having a socket formed in one end thereof;
   a plunger assembly, said plunger assembly including a plunger member disposed in said socket and moving independently of said body; and a detent member located on said body, said detent member movable between a first and a second position wherein positioning said detent member in said second position operates to secure said body from movement relative to a bone nail;

said second position of said detent member includes at least a portion of said detent member radially displaced and extending outwardly above an outer surface of said body; and said detent member includes an outer surface, said outer surface configured to engage the bone nail, said outer surface having an irregular configuration to increase a holding force and correspondingly reduce movement of the body with respect to the bone nail.

2. An apparatus as set forth in claim 1 including a drive assembly, said drive assembly operative to engage said detent member and move said detent member towards said second position.

3. An apparatus as set forth in claim 2 wherein said drive assembly includes a threaded member.

4. An apparatus as set forth in claim 3 including said body having a threaded bore and said threaded member located in said threaded bore wherein rotation of said threaded member in said threaded bore moves said detent member towards said second position.

5. An apparatus as set forth in claim 1 wherein said irregular configuration includes a plurality of ridges and grooves located on said outer surface.

6. An apparatus as set forth in claim 1 wherein said irregular configuration includes a surface coating located on said outer surface.

7. An apparatus as set forth in claim 1 including a drive assembly, said drive assembly operative to engage said detent member and move said detent member toward said second position.

8. An apparatus as set forth in claim 7 wherein said drive assembly engages said detent member and operates to drive a portion of the outer surface of said detent member outwardly past an outer peripheral surface of the body.

9. An apparatus as set forth in claim 1 including said detent member having a fixed end and a free end, said fixed end secured to said body.

10. An apparatus as set forth in claim 1 wherein said detent member includes a cantilevered member, said cantilevered member connected to said body.

11. An apparatus as set forth in claim 10 wherein said cantilevered member includes a free end and a fixed end wherein the thickness of the cantilevered member is greater at the free end than at the fixed end.

12. An apparatus as set forth in claim 11 wherein said cantilevered member includes a threaded inner surface; said body having a threaded bore; and a threaded member located in said threaded bore wherein rotation of said threaded member in said threaded bore moves said detent member towards said second position.

13. An apparatus as set forth in claim 12 wherein said plunger assembly includes a spring member, a guide member and a retainer.

14. A bone screw for use in combination with a bone nail to treat a bone fracture comprising:

a body, said body having a socket formed in one end thereof;

a detent member located on said body, said detent member movable between a first and a second position wherein said second position of said detent member includes at least a portion of said detent member extending above an outer surface of said body whereby positioning said detent member in said second position operates to secure said body from movement relative to the bone nail;

a drive member operative to engage said detent member and move said detent member towards said second position; and a plunger assembly, said plunger assembly including a threaded plunger disposed in a socket formed in one end of said body; and a spring member located between said threaded plunger and said body.

15. A bone screw as set forth in claim 14 wherein said body includes a threaded bore; and said drive member includes a threaded member located in said threaded bore such that rotation of said threaded member in said threaded bore moves said detent member towards said second position.

16. A bone screw as set forth in claim 14 wherein said detent member includes an outer surface, said outer surface engaging said bone nail when said detent member is moved to said second position, said outer surface configured to increase the holding force and correspondingly reduce movement of the body with respect to the bone nail.

17. A bone screw as set forth in claim 14 wherein said detent member includes a cantilevered member, said cantilevered member connected to said body, said cantilevered member having a free end and a fixed end wherein a thickness of the cantilevered member is greater at the free end then at the fixed end.

18. An apparatus for repairing a bone fracture comprising:

a body;

a detent assembly on said body, said detent assembly movable between a first and a second position wherein positioning said detent assembly in said second position operates to secure said body from movement;

said detent assembly including a detent member and a drive member, said drive member operative to engage said detent member and move said detent member towards said second position;

said second position of said detent member includes at least a portion of said detent member radially displaced and extending outwardly above an outer surface of said body; and said detent member having an irregular outer surface, at least a portion of said irregular outer surface spaced from and extending radially outward of said outer surface of said body when said detent assembly is in said second position.

* * * * *